US006329501B1

(12) United States Patent
Smith et al.

(10) Patent No.: US 6,329,501 B1
(45) Date of Patent: Dec. 11, 2001

(54) METHODS AND COMPOSITIONS FOR TARGETING COMPOUNDS TO MUSCLE

(75) Inventors: Bruce F. Smith; Tatiana Samoilova, both of Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 09/084,605

(22) Filed: May 26, 1998

Related U.S. Application Data

(60) Provisional application No. 60/047,863, filed on May 29, 1997.

(51) Int. Cl.$^7$ .................................................. C07K 4/00
(52) U.S. Cl. ......................... 530/329; 530/328; 530/327; 530/326; 530/300
(58) Field of Search .................. 530/300.358, 387.1, 530/388.1; 435/7.1; 424/93.6

(56) References Cited

U.S. PATENT DOCUMENTS

| | | | |
|---|---|---|---|
| 4,879,216 | * 11/1989 | Hallermayer et al. | 435/7 |
| 5,622,699 | 4/1997 | Ruoslahti et al. | 424/93.6 |
| 5,846,773 | * 12/1998 | Lee et al. | 435/69.1 |

OTHER PUBLICATIONS

Beri et al. (1987; Nucleic Acids Res. 15:7991–8001).*
Yamamoto et al. (1996; DNA Res. 3:257–262).*
PCT International Search Report, PCT/US98/10815, dated Sep. 28, 1998.
Pasqualini et al. (Mar. 28, 1996), "Organ Targeting In Vivo Using Phage Display Peptide Libraries", *Nature 380:* 364–366.
Feero et al. (Feb. 1996), "Toward Systemic Gene Delivery For Duchenne Muscular Dystrophy: Transferrin As A Muscle Targeting Ligand", *Neurology 46(2):*A390, S42.003.
Cruz et al. (1985), "Conus Geographus Toxins That Discriminate Between Neuronal and Muscle Sodium Channels", *The Journal of Biological Chemistry 260(16):*9280–9288.
Russell (Mar. 1996), "Peptide–Displaying Phages For Targeted Gene Delivery", *Nature Medicine 2(3):*276–277.
Barry et al. (Mar. 1996), "Toward Cell–Targeting Gene Therapy Vectors: Selection of Cell–Binding Peptides From Random Peptide–Presenting Phage Libraries", *Nature Medicine 2(3):*299–305.
Polgren et al. (1997), "Identification of Muscle Homing Sequences By Using Phage Display Libraries of Peptides", *Tumor Biology 18(Supplement 1):*77.
Schumacher et al. (Mar. 1996), "Identification of D–Peptide Ligands Through Mirror–Image Phage Display", *Science 271:*1854–1857.
Cwirla et al. (1990), "Peptides On Phage: A Vast Library Of Peptides For Identifying Ligands", *Proc. Nat'l Acad. Sci. USA 87:*6378–6382.
Wu et al. (1991), "Receptor–Mediated Gene Delivery In Vivo", *The Journal of Biological Chemistry 266(22):*14338–14342.
Wu et al. (1988), "Receptor–Mediated Gene Delivery and Expression In Vivo", *The Journal of Biological Chemistry 263(29):*14621–14624.
Wu et al. (1989), "Targeting Genes: Delivery and Persistent Expression of a Foreign Gene Driven by Mammalian Regulatory Elements In Vivo", *The Journal of Biological Chemistry 264(29):*16985–16987.
Zenke et al. (1990), "Receptor–Mediated Endocytosis of Transferrin–Polycation Conjugates: An Efficient Way To Introduce DNA Into Hematopoietic Cells", *Proc. Nat'l Acad. Sci. USA 87:*3655–3659.
Wagner et al. (1990), "Transferrin–Polycation Conjugates As Carriers For DNA Uptake Into Cells", *Proc. Nat'l Acad. Sci. USA 87:*3410–3414.
Barr et al. (1991), "Systemic Delivery of Recombinant Proteins By Genetically Modified Myoblasts", *Science 254:*1507–1509.
Velez–Yanguas et al. (1996), "The Evolution of Chemotherapeutic Agents for the Treatment of Pediatric Musculoskeletal Malignancies", *The Orthopedic Clinics of North America 27(3):*545–549.
Douglas et al. (1995), "Targeted Gene Therapy", *Tumor Targeting 1(2):*67–84.
Le Bricon et al. (1995), "Negative Impact of Cancer Chemotherapy on Protein Metabolism in Healthy and Tumor–Bearing Rats", *Metabolism 44(10):*1340–1348.
England et al. (1990), "Very Mild Muscular Dystrophy Associated With the Deletion of 46% of Dystrophin", *Nature 343(6254):*180–182.
Haeckher et al. (1996), "In Vivo Expression of Full–Length Human Dystrophin From Adenoviral Vectors Deleted of All Viral Genes", *Human Gene Therapy 7:*1907–1914.
Devlin et al. (1990), "Random Peptide Libraries: A Source of Specific Protein Binding Molecules", *Science 249:*404–406.

* cited by examiner

*Primary Examiner*—Karen Cochrane Carlson
(74) *Attorney, Agent, or Firm*—Alston & Bird LLP (57) ABSTRACT

Compositions for use in targeting therapies to muscle cells are provided. The compositions comprise peptides which are capable of binding muscle cells in vivo.

7 Claims, 3 Drawing Sheets

Results: The sequence WDR NGK T is common for all sets; SGL PAY P is common for two sets. Set #1 has four identical sequences. Set #2 has four identical sequences. Red sequences from set #1 and set #2 have four identical amino acids. Two of them (S and I) take the same positions. Set #3 has no identical sequences.

SEQUENCE LISTING

```
<160> NUMBER OF SEQ ID NOS:  29

<210> SEQ ID NO 1
<211> LENGTH: 7
<212> TYPE: PRT
<213> ORGANISM: Artificial Sequence
<220> FEATURE:
<223> OTHER INFORMATION: Phage display library peptides
```

```
<400> SEQUENCE: 1

Trp Asp Ala Asn Gly Lys Thr
 1               5

<210> SEQ ID NO 2
<211> LENGTH: 7
<212> TYPE: PRT
<213> ORGANISM: Artificial Sequence
<220> FEATURE:
<223> OTHER INFORMATION: Phage display library peptides

<400> SEQUENCE: 2

Ala Ser Ser Leu Asn Ile Ala
 1               5

<210> SEQ ID NO 3
<211> LENGTH: 7
<212> TYPE: PRT
<213> ORGANISM: Artificial Sequence
<220> FEATURE:
<223> OTHER INFORMATION: Phage display library peptides

<400> SEQUENCE: 3

Leu Ala Pro Gln Lys Leu Pro
 1               5

<210> SEQ ID NO 4
<211> LENGTH: 7
<212> TYPE: PRT
<213> ORGANISM: Artificial Sequence
<220> FEATURE:
<223> OTHER INFORMATION: Phage display library peptides

<400> SEQUENCE: 4

Val Ser Ala Ala Pro Tyr Pro
 1               5

<210> SEQ ID NO 5
<211> LENGTH: 7
<212> TYPE: PRT
<213> ORGANISM: Artificial Sequence
<220> FEATURE:
<223> OTHER INFORMATION: Phage display library peptides

<400> SEQUENCE: 5

Ala Ala Ala Asn Val Trp His
 1               5

<210> SEQ ID NO 6
<211> LENGTH: 7
<212> TYPE: PRT
<213> ORGANISM: Artificial Sequence
<220> FEATURE:
<223> OTHER INFORMATION: Phage display library peptides

<400> SEQUENCE: 6

Ala Tyr Pro Gly Phe Ala Leu
 1               5

<210> SEQ ID NO 7
<211> LENGTH: 7
<212> TYPE: PRT
<213> ORGANISM: Artificial Sequence
<220> FEATURE:
<223> OTHER INFORMATION: Phage display library peptides

<400> SEQUENCE: 7
```

Thr Ala Thr Ile Thr Thr Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Phage display library peptides

<400> SEQUENCE: 8

Met Ser Thr Gln Ser Ile Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Phage display library peptides

<400> SEQUENCE: 9

Ser Gly Leu Pro Ala Tyr Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Phage display library peptides

<400> SEQUENCE: 10

Ala Gly Met Ala His Ile Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Phage display library peptides
<221> NAME/KEY: VARIANT
<222> LOCATION: (1)...(7)
<223> OTHER INFORMATION: Xaa = Any Amino Acid

<400> SEQUENCE: 11

Ser Thr Ser Xaa Ile Thr His
1               5

<210> SEQ ID NO 12
<211> LENGTH: 7
<212> TYPE: PRT
<213> ORGANISM: Artificial Sequence
<220> FEATURE:
<223> OTHER INFORMATION: Phage display library peptides

<400> SEQUENCE: 12

Ser Tyr Phe Ser Ala Pro Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Phage display library peptides

```
<400> SEQUENCE: 13

Gln Leu Ser Leu Leu Leu Ala
 1               5

<210> SEQ ID NO 14
<211> LENGTH: 7
<212> TYPE: PRT
<213> ORGANISM: Artificial Sequence
<220> FEATURE:
<223> OTHER INFORMATION: Phage display library peptides

<400> SEQUENCE: 14

Trp Lys Pro Ala Thr Phe Tyr
 1               5

<210> SEQ ID NO 15
<211> LENGTH: 7
<212> TYPE: PRT
<213> ORGANISM: Artificial Sequence
<220> FEATURE:
<223> OTHER INFORMATION: Phage display library peptides

<400> SEQUENCE: 15

Ala Pro Leu Tyr Pro Pro Ser
 1               5

<210> SEQ ID NO 16
<211> LENGTH: 7
<212> TYPE: PRT
<213> ORGANISM: Artificial Sequence
<220> FEATURE:
<223> OTHER INFORMATION: Phage display library peptides

<400> SEQUENCE: 16

His Leu Ser Asn Trp Pro Arg
 1               5

<210> SEQ ID NO 17
<211> LENGTH: 7
<212> TYPE: PRT
<213> ORGANISM: Artificial Sequence
<220> FEATURE:
<223> OTHER INFORMATION: Phage display library peptides

<400> SEQUENCE: 17

Ser Met Gln Thr His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Phage display library peptides

<400> SEQUENCE: 18

Ser His Trp His Asn Ser Glu
 1               5

<210> SEQ ID NO 19
<211> LENGTH: 7
<212> TYPE: PRT
<213> ORGANISM: Artificial Sequence
<220> FEATURE:
<223> OTHER INFORMATION: Phage display library peptides
```

```
<400> SEQUENCE: 19

His Pro Ala His Val Ala Lys
 1               5

<210> SEQ ID NO 20
<211> LENGTH: 7
<212> TYPE: PRT
<213> ORGANISM: Artificial Sequence
<220> FEATURE:
<223> OTHER INFORMATION: Phage display library peptides

<400> SEQUENCE: 20

Thr Thr Gln His Met Leu Lys
 1               5

<210> SEQ ID NO 21
<211> LENGTH: 9
<212> TYPE: PRT
<213> ORGANISM: Artificial Sequence
<220> FEATURE:
<223> OTHER INFORMATION: Phage display library peptides

<400> SEQUENCE: 21

Cys Gly His His Pro Val Tyr Ala Cys
 1               5

<210> SEQ ID NO 22
<211> LENGTH: 7
<212> TYPE: PRT
<213> ORGANISM: Artificial Sequence
<220> FEATURE:
<223> OTHER INFORMATION: Phage display library peptides

<400> SEQUENCE: 22

Ser Gly Thr Leu Phe Ala Asn
 1               5

<210> SEQ ID NO 23
<211> LENGTH: 7
<212> TYPE: PRT
<213> ORGANISM: Artificial Sequence
<220> FEATURE:
<223> OTHER INFORMATION: Phage display library peptides

<400> SEQUENCE: 23

Lys Ala Pro Leu Thr Pro Val
 1               5

<210> SEQ ID NO 24
<211> LENGTH: 7
<212> TYPE: PRT
<213> ORGANISM: Artificial Sequence
<220> FEATURE:
<223> OTHER INFORMATION: Phage display library peptides

<400> SEQUENCE: 24

Gln Trp His Gly Pro Leu His
 1               5

<210> SEQ ID NO 25
<211> LENGTH: 7
<212> TYPE: PRT
<213> ORGANISM: Artificial Sequence
<220> FEATURE:
<223> OTHER INFORMATION: Phage display library peptides

<400> SEQUENCE: 25
```

His Val His Thr Leu Pro Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Phage display library peptides

<400> SEQUENCE: 26

Met His His Thr Arg Phe Tyr
1               5

<210> SEQ ID NO 27
<211> LENGTH: 7
<212> TYPE: PRT
<213> ORGANISM: Artificial Sequence
<220> FEATURE:
<223> OTHER INFORMATION: Phage display library peptides

<400> SEQUENCE: 27

Ala Pro Val His Arg Pro Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Phage display library peptides

<400> SEQUENCE: 28

His Ala Ile Tyr Pro Arg His
1               5

<210> SEQ ID NO 29
<211> LENGTH: 7
<212> TYPE: PRT
<213> ORGANISM: Artificial Sequence
<220> FEATURE:
<223> OTHER INFORMATION: Phage display library peptides

<400> SEQUENCE: 29

Gly Glu Thr Arg Ala Pro Leu
1               5

US 6,329,501 B1

METHODS AND COMPOSITIONS FOR TARGETING COMPOUNDS TO MUSCLE

This application claims the benefit of provisional application Ser. No. 60/047,863 filed May 29, 1997, which disclosure is herein incorporated.

FIELD OF THE INVENTION

The invention relates to methods for gene therapy, particularly for targeting genes, proteins, pharmaceuticals, or other compounds to muscle.

BACKGROUND OF THE INVENTION

The capabilities to introduce a particular foreign or native gene sequence into a mammal and to control the expression of that gene are of substantial value in the fields of medical and biological research. Such capabilities provide a means for studying gene regulation and for designing a therapeutic basis for the treatment of disease.

In addition to introducing the gene into mammals, providing expression of the gene at the site of interest remains a challenge. Methods have been developed to deliver DNA to target cells by capitalizing on indigenous cellular pathways of macromolecular transport. In this regard, gene transfer has been accomplished via the receptor-mediated encytosis pathway employing molecular conjugate vectors.

Inherited diseases of muscle pose a therapeutic challenge, as muscle is the single largest tissue of the body. Pharmacologic approaches do not significantly alter the course of many of these diseases as such approaches fail to correct the underlying genetic deficit. New approaches, relying on the transfer of genetic material have been advocated. However, current methodologies used for gene therapy are limited in their usefulness with regard to treating myopathies. Local administration of gene therapy vectors or transplantation of donor cells only treat the immediate area of the injection site. Effective therapy with these methods requires multiple injections and carry the safety risks associated with disease transplantation and the use of immunosuppressive drugs.

Duchenne muscular dystrophy is probably the most common inherited progressive lethal disorder of mankind. The rate of occurrence of the disease is attributable to the very high mutation rate of the gene. The progression of the clinical disease is characterized by skeletal muscle tissue deterioration and wasting. Duchenne muscular dystrophy (DMD) follows a degenerative course which confines sufferers to a wheelchair by the age of about 12 years old and results in death by the third decade due to cardiac or respiratory failure.

DMD results from mutations, mainly frame-shift deletions, in a single, recessively inherited gene. The gene has been cloned and represents the largest gene so far identified in the human genome, spanning at least 2.3 megabases in the short arm of the X chromosome.

Positional cloning of the X-linked gene has revealed that defects of the dystrophin gene lead to either Duchenne or Becker muscular dystrophy (BMD). The 14 kilobase (kb) dystrophin mRNA encodes a 3685 amino acid protein of 427 kilodaltons (kD) with overall similarity to the cytoskeletal proteins β-spectrin and α-actinin. These proteins perform structural roles in static and dynamic cellular processes and all cell types. Dystrophin is associated with the cytoplasmic face of the sarcolemma and is thus an essential component of the muscle cytoskeleton. Although the exact function of dystrophin is unknown, it has been postulated to contribute to stabilization of the sarcolemma.

The current approaches to the in vivo transfer of dystrophin cDNA for the treatment of DMD have involved direct intramuscular injection of naked plasmid DNA or recombinant viral vectors. However, these techniques suffer from the limitation that skeletal muscle comprises a large proportion of the cells of the body, making widespread intramuscular transduction impractical in a clinical context. Furthermore, some muscles affected in DMD, such as the heart and diaphragm, are not readily accessable to direct injection.

Current approaches to gene therapy in inherited myopathies are limited in practicality either by the mode of administration or the capacity of the vector used for gene transfer. Therefore, methods are needed for targeting specific compositions to muscle cells.

SUMMARY OF THE INVENTION

Compositions and methods for targeting genes, proteins, pharmaceuticals, or other compounds to muscle are provided. The compositions comprise peptide sequences which bind muscle, in vivo, with high specificity. Both species-specific and species-independent sequences have been determined.

The compositions are useful in gene therapy methods for the treatment of myopathies, gene therapy of disease where muscles potentially serve as reservoirs of protein production, and delivery of a wide variety of drugs to muscles.

DETAILED DESCRIPTION OF THE INVENTION

The invention is drawn to peptide sequences that are capable of binding muscle with high specificity. Both species-specific and species-independent peptide sequences have been identified. The peptide sequences are useful for targeting components to muscle.

The peptides of the invention are generally short peptide ligands. The peptide ligands exhibit at least three-fold, preferably ten-fold, more preferably greater than ten-fold binding affinity for muscle cells.

The peptides of the invention are cell-binding and cell-entry peptides. For the most part, the peptides will comprise at least about 5 to about 50 amino acids, preferably at least about 5 to about 30 amino acids, more preferably at least about 7 to about 20 amino acids. It is recognized that consensus sequences may be identified among the peptides that are capable of binding to a target. Such consensus sequences identify key amino acids or patterns of amino acids that are essential for binding. Consensus sequences may be determined by an analysis of peptide patterns that are capable of binding muscle cells. Once recognized the consensus regions will be used in constructing other peptides for use in muscular targeting. Such consensus sequences may be tested by constructing peptides and determining the effect of the consensus sequence on binding. In this manner, as long as the consensus sequence is present, the peptide will bind the target. In some cases, longer peptides will be useful as such peptides may be more easily bound or more readily enter into the target cell.

The peptides can be classified into linear, cyclic and conformational types. While the invention is not bound by any particular mode of action, it is postulated that the shorter peptides, generally from about 7 to about 20 amino acids are involved in linear binding to the target muscle cells. Longer peptides assume conformational folding and are involved in conformational binding. Cyclic peptide structures can also be constructed for use in the invention. In this manner, a core peptide region such as a consensus peptide binding sequence will be flanked with identical sequences to form cyclic peptides. Such libraries are available commercially, for example the Ph.D.™ Phage display peptide library kits from New England Biolabs, Inc. See also, Parmley et al. (1988) *Gene* 73:305–318; Cortese et al. (1995) *Curr. Opin. Biotechnol* 6:73–80; Noren (1996) *NEB Transcript* 8(1):1–5; and Devlin et al. (1990) *Science* 249:404–406.

Peptides of the invention can be determined which are capable of binding any type of muscle cells including skeletal, smooth, cardiac, and the like. Based on the selective binding protocols, peptides which are tissue or muscle-type specific or alternatively which are capable of binding to different muscle cells can be determined. In the same manner, the peptides may be species independent, that is, the peptides will bind to the muscle type from any mammalian species. Alternatively, the peptides may be species specific. By species specific is intended that peptides are specific for muscle cells from a particular species and will not bind to muscle cells from another species. Therefore, the peptides may be characterized by tissue specificity or alternatively by species specificity. Mammalian species of interest include, but are not limited to human, rat, dog, chimpanzee, etc.

Multiple muscle targets can be utilized to select for muscle-binding peptides. Peptides can be selected against differentiated myotube cell lines from any mammal, as well as against primary muscle samples from mammals, including quadracep, tibialis anterior, soleus, cardiac, and the like.

Methods are available in the art for the determination of the peptides of the invention. Such methods include selection from a bacteriophage library which expresses random peptides, mirror image phage display to isolate naturally-occurring L-enantiomers in a peptide library, and the like. See, for example, Barry et al. (1996) *Nature Medicine* 2:299–305; Schumacher et al. (1996) *Science* 271:1854–1857; Pasqualini et al. (1996) *Nature* 380:364–366; and the references cited therein, herein incorporated by reference.

Peptides of the invention can be determined from phage libraries which have been used to select random peptides that bind single proteins. See, Barry et al. (1996) *Nature Medicine* 2:299–305; Devlin et al. (1990) 249:404–406; Cwirla et al. (1990) *Proc. Natl. Acad. Sci. USA* 87:6378–6382; and the references cited therein. In this manner, peptide libraries can be constructed utilizing a number of random amino acids. The random amino acids are fused to the amino terminus of a phage protein and expressed as a bacteriophage library. See, Barry et al. (1996) *Nature Medicine* 2:299–305, herein incorporated by reference. The phage is hybridized to the cells of interest, at different temperatures, generally about 4° C. and about 37° C. After repeated selection, peptides which exhibit a higher affinity for the cells of interest are isolated. Methods for preparing libraries containing diverse populations are also disclosed in Gordon et al. (1994) *J. Med. Chem.* 37:1385–1401; Ecker and Crooke (1995) *BioTechnology* 13:351–360; Goodman and Ro, Peptidomimetics For Drug Design, in "Burger's Medicinal Chemistry and Drug Discovery", Vol. 1, M. E. Wolff (Ed.) John Wiley & Sons 1995, pages 803–861; Blondelle et al. (1995) *Trends Anal. Chem.* 14:83–92; and Sambrook et al., Molecular Cloning: A Laboratory Manual, Cold Spring Harbor Press, 1989. Each of these references are herein incorporated by reference.

After in vitro screening of the peptides, the peptides of the invention are selected based on in vivo binding. Such methods for in vivo binding are known in the art. See, for example, Pasqualini et al. (1996) *Nature* 380:364–366, and the references cited therein. While the invention is discussed in terms of peptides, it is recognized that other molecules may be identified in the same manner. Such molecules include organic chemicals, modified peptides, proteins such as antibodies, antibody fragments, and the like.

The screening method of the invention comprises administering a library of molecules to the muscle cells of interest and identifying those molecules which are capable of binding. See, for example, U.S. Pat. No. 5,622,699, herein incorporated by reference.

For peptides capable of binding human muscle cells, chimpanzees can be used as the target mammal. Thus, species independent peptides can be identified which do not cross react with other mammalian species. For peptides which cross-react or are species independent, after screening in a first mammal, the peptides are screened in at least a second mammal and those which bind can be determined. As noted above, because the mammal is typically sacrificed to determine binding, a primate species can be used for human, generally chimpanzees.

The in vivo selection method of the invention represents the first methods where peptides have been determined which bind differentiated or "adult" muscle. Previous attempts have selected based on muscle cells in tissue culture. Muscle cells in culture are not characteristic of adult muscle even if collected from developed muscle. Once the cells are cultured they convert to an embryonic phenotype. See Gambke et al. (1984) *J. Biol Chem.* 259:12092–12100. Thus, the peptides of the invention have different binding specificities and affinities. It is using the methods of the invention that tissue and species-independent peptides can be determined.

Once peptides have been selected which show an affinity for the target tissue, they may be modified by methods known in the art. Such methods include random mutagenesis, as well as synthesis of the compounds for selected amino acid substitutions. Peptides of various length can be constructed and tested for the effect on binding affinity and specificity. In this manner, the binding affinity may be increased or altered. Thus, peptides may be identified which exhibit specific binding to muscle cells, as well as peptides which exhibit specific binding and internalization by the muscle cells of interest.

The peptides find use in targeting genes, proteins, pharmaceuticals, or other compounds to particular muscle tissue. In this manner, the peptides can be used in any vector systems for delivery of specific nucleotides or compositions to the target cells. By nucleotide is intended gene sequences, DNA, RNA, as well as antisence nucleic acids.

The nucleotide sequences encoding the muscle-specific peptides are also encompassed. Where necessary, the nucleotide sequences can be used in the construction of fusion proteins or vectors for use in the invention. Such methods are known in the art. Additionally the construction of expression cassettes are known as well as promoters, terminators, enhancers, etc., necessary for expression.

A number of vector systems are known for the introduction of foreign or native genes into mammalian cells. These include SV40 virus (See, e.g., Okayama et al. (1985) *Mol. Cell Biol.* 5:1136–1142); Bovine papilloma virus (See, e.g., DiMaio et al. (1982) *Proc. Natl. Acad Sci. USA* 79:4030–4034); adenovirus (See, e.g., Morin et al. (1987) *Proc. Natl. Acad. Sci. USA* 84:4626; Yifan et al. (1995) *Proc. Natl. Acad. Sci. USA* 92:1401–1405; Yang et al. (1996) *Gene Ther.* 3:137–144; Tripathy et al. (1996) *Nat. Med.* 2:545–550; Quantin et al. (1992) *Proc. Natl. Acad. Sci. USA* 89:2581–2584; Rosenfeld et al. (1991) *Science* 252:431–434; Wagner (1992) *Proc. Natl. Acad Sci. USA* 89:6099–6103; Curiel et al. (1992) *Human Gene Therapy* 3:147–154; Curiel (1991) *Proc. Natl. Acad. Sci. USA* 88:8850–8854; LeGal LaSalle et al. (1993) *Science* 259:590–599); Kass-Eisler et al. (1993) *Proc. Natl. Acad. Sci. USA* 90:11498–11502); adeno-associated virus (See, e.g., Muzyczka et al. (1994) *J. Clin. Invest.* 94:1351; Xiao et al. (1996) *J. Virol.* 70:8098–8108); herpes simplex virus (See, e.g., Geller et al. (1988) *Science* 241:1667; Huard et al. (1995) *Gene Therapy* 2:385–392; U.S. Pat. No. 5,501,979); retrovirus-based vectors (See, for example, Curran et al. (1982) *J. Virol.* 44:674–682; Gazit et al. (1986) *J Virol.* 60:19–28; Miller, A. D. (1992) *Curr. Top. Microbiol. Immunol.* 158:1–24; Cavanaugh et al. (1994) *Proc. Natl. Acad. Sci. USA* 91:7071–7075; Smith et al. (1990) *Mol. Cell. Biol.* 10:3268–3271); herein incorporated by reference.

In the same manner, the peptides can be used in any mammalian expression vector to target the expression system to the appropriate target muscle cells. See, for example, Wu et al. (1991) *J. Biol. Chem.* 266:14338–14342; Wu and Wu (*J. Biol Chem.* (1988)) 263:14621–14624; Wu et al. (1989) *J. Biol. Chem.* 264:16985–16987; Zenke et al. (1990) *Proc. Natl. Acad. Sci. USA* 87:3655–3659; Wagner et al. (1990) 87:3410–3414.

Standard techniques for the construction of the vectors of the present invention are well-known to those of ordinary skill in the art and can be found in such references as Sambrook et al., *Molecular Cloning: A Laboratory Manual*, 2nd ed. (Cold Spring Harbor, New York, 1989). A variety of strategies are available for ligating fragments of DNA, the choice of which depends on the nature of the termini of the DNA fragments and which choices can be readily made by those of skill in the art.

Where the peptides of the invention are targeting a gene for expression in muscles, the gene to be expressed will be provided in an expression cassette with the appropriate regulatory elements necessary for expression of the gene. Such regulatory elements are well known in the art and include promoters, terminators, enhancers, etc.

The peptides of the invention may also be utilized to target liposomes, polylysine, or other polycation conjugates, and synthetic molecules. See, for example, de Haan et al. 91996) *Immunology* 89:488–493; Gorlach et al. (1996) DTWDTsch *Tierarytl Wochenschr* 103:312–315; Benameur et al. (1995) *J. Phar. Pharmacol.* 47:812–817; Bonanomi et al. (1987) *J. Microencapsul* 4:189–200; Zekorn et al. (1995) *Transplant Proc.* 27:3362–3363.

In this manner, the peptides of the invention can be used to provide therapies for neuromuscular and muscular diseases, including Duchenne muscular dystrophy, Becker muscular dystrophy, myotic dystrophy, myotiona congenita, dermatomyositis, polymyositis, polyneuropathy, and other myopathies. That is, genes proteins, or pharmaceuticals can be directed to muscles in those patients suffering from the particular disease.

Peptides of the invention also find use in treating cardiac diseases and in targeting drugs to the heart. See, for example, Onodera et al. (1997) *Transplant Proc.* 29:1907–1908; Langtry (1997) *Drugs* 53:867–884; Donahue (1997) *Proc. Natl. Acad. Sci. USA* 94:4664–4668; Kass-Eisler et al. (1993) *Proc. Natl. Acad. Sci. USA* 90:11498–11502; Guzman et al. (1993) *Circ. Res.* 73:1202–1207; Barr et al. (1994) *Gene Ther.* 1:51–58; Gojo et al. (1997) *J. Ther. Cardiovas. Surg.* 113:10–18; March et al. (1995) *Hum Gene. Ther.* 6:41–53; Villarreal et al. (1996) *J. Mol. Cell Cardiol.* 28:735–742; Wang et al. (1996 *Transplantation* 61:1726–1729; Lee et al. (1996)*J. Thorac Cardiovasc. Surg.* 111:246–252; and the references cited therein.

In this manner, cardiac peptide directed therapies are useful for the treatment of a number of acquired and inherited cardiovascular diseases. Previous gene transfer approaches have been limited by relatively low efficiencies of gene transduction. Thus, the present approach provides a means to increase recombinant gene expression and pharmaceutical concentration in the muscular layers of the coronary arteries as well as the myocardium.

The compositions of the invention may be provided as pharmaceutical formulations suitable for parenteral (e.g., subcutaneous, intradermal, intramuscular, intravenous and intraarticular), oral or inhalation administration. Alternatively, pharmaceutical formulations of the present invention may be suitable for administration to the mucous membranes of the subject (e.g., intranasal administration). The formulations may be conveniently prepared in unit dosage form and may be prepared by any of the methods well-known in the art.

Any inert pharmaceutically-acceptable carrier may be used, such as saline, or phosphate-buffered saline, or any such carrier in which the compositions of the present invention have suitable solubility properties for use in the methods of the present invention. Reference is made to Remington's Pharmaceutical Sciences, Merck Publishing Company Easton, Pa., Osol (ed.) (1980) for methods of formulating pharmaceutical compositions.

The peptides of the invention may also be utilized for gene therapy of disease where muscles may serve as a reservoir of protein production, such as diabetes, hemophilia, and the like. Proteins which can be delivered include hGH (Dhawan et al. (1991) *Science* 254:1509–1512); factor 1X protein (Dai et al. (1992) *Proc. Natl. Acad. Sci. USA* 89:10892–10895; Yas et al. (1992) *Proc. Natl. Acad. Sci. USA* 89:3357–3361; and Roman et al. (1992) *Somatic Cell and Molecular Genetics* 18:247–258) insulin; and the like. See, generally, Barr et al. (1991) *Science* 245:1507–1509.

In the same manner, the peptides of the invention may be utilized to target pharmaceuticals and chemotherapeutic agents to treat muscle disease such as cancers or tumors of muscle origin. See, for example, Velez-Yanguas et al. (1996) *Orthop. Clin. North Am.* 27:545–549; Douglas et al. (1995) *Tumor Targeting* 1:67–84; and LeBricon (1995) *Metabolism* 44:1340–1348.

In one example of methods of the invention, the peptides are utilized in a vector system as the ligand-binding domain for the treatment of muscular disease, particularly DMD. The method provides intravenous injection of an expression vector comprising the targeting peptides of the invention operably linked with an expression cassette comprising the Duchenne dystrophy gene to deliver the dystrophin product to the muscles.

Because of the insert size limitations of most retroviral and adenoviral vectors, they may be incapable of accommodating the 14 kb full-length dystrophin cDNA. In these cases, a 6.3 kb dystrophin cDNA may be utilized and expressed in the vector. See, England et al. (1990) *Nature* 343:180–182.

Alternatively, adenovirus vectors are known in the art which are capable of expressing the full-length DMD gene. See, for example, Haeker et al. (1996) *Human Gene Therapy* 7:1907–1914, which discloses the expression of full-length human dystrophin from an adenoviral vector which has all viral genes deleted. The peptides of the invention could be used to direct such a vector system to skeletal muscle.

The following experiments are offered by way of illustration and not by way of limitation.

EXPERIMENTAL

Example 1

Figure 1:
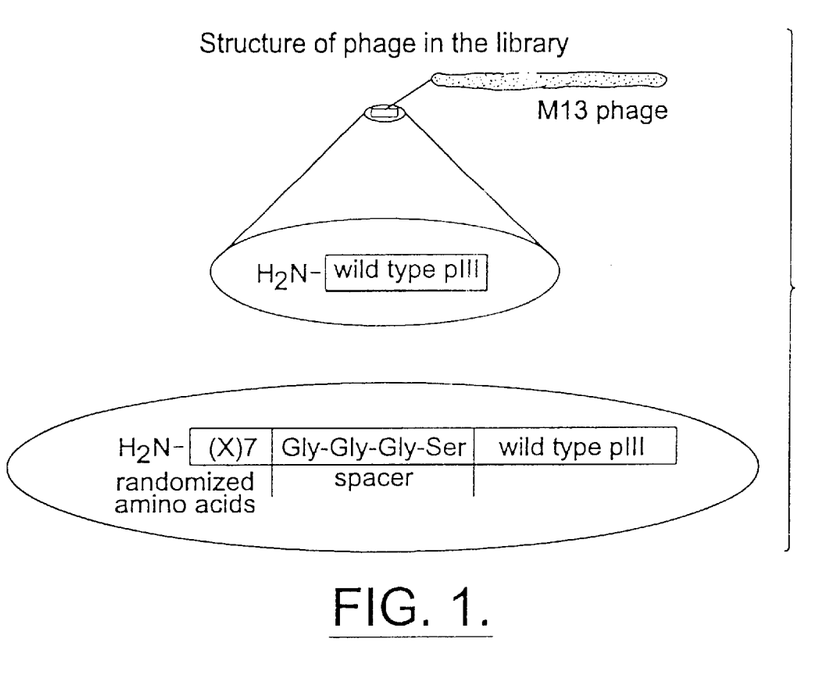
FIG. 1 provides the structure of phage in the library.

Phase Presentation Libraries May be Utilized to Identify Novel Ligands for Gene Transfer to Muscle A key factor in any targeting schema is the availability of appropriate specific molecules on the target cells which can be exploited. Of note in this regard, the available ligands for targeting muscle were until recently limited in number and functional applicability. Many markers of skeletal muscle were described during studies of differentiation and therefore are only expressed in myoblasts, mononuclear myocytes, and immature myotubes. However, if skeletal muscle is to be rescued from degeneration due to the absence of dystrophin, mature adult myotubes must be targeted. Thus, the identification of cell surface markers specific to mature myotubes is of critical importance to the implementation of the gene delivery strategies for the treatment of DMD. Systems which, while utilizing a variety of different approaches, fundamentally share the similarity of examining libraries of peptides for their ability to bind to specific cell types, both in vitro and in vivo are useful. See, FIG. 1 which sets forth the structure of phage in the library.

Example 2

Selection of Peptides against Myoblasts and Myotubes

For MD gene therapy, muscle cells will need to be targeted. Candidate muscle-binding peptides are selected by panning against $C_2C_{12}$ myotubes (Barry et al. (1996) *Mature Medicine* 2:299–305).

Figure 2:
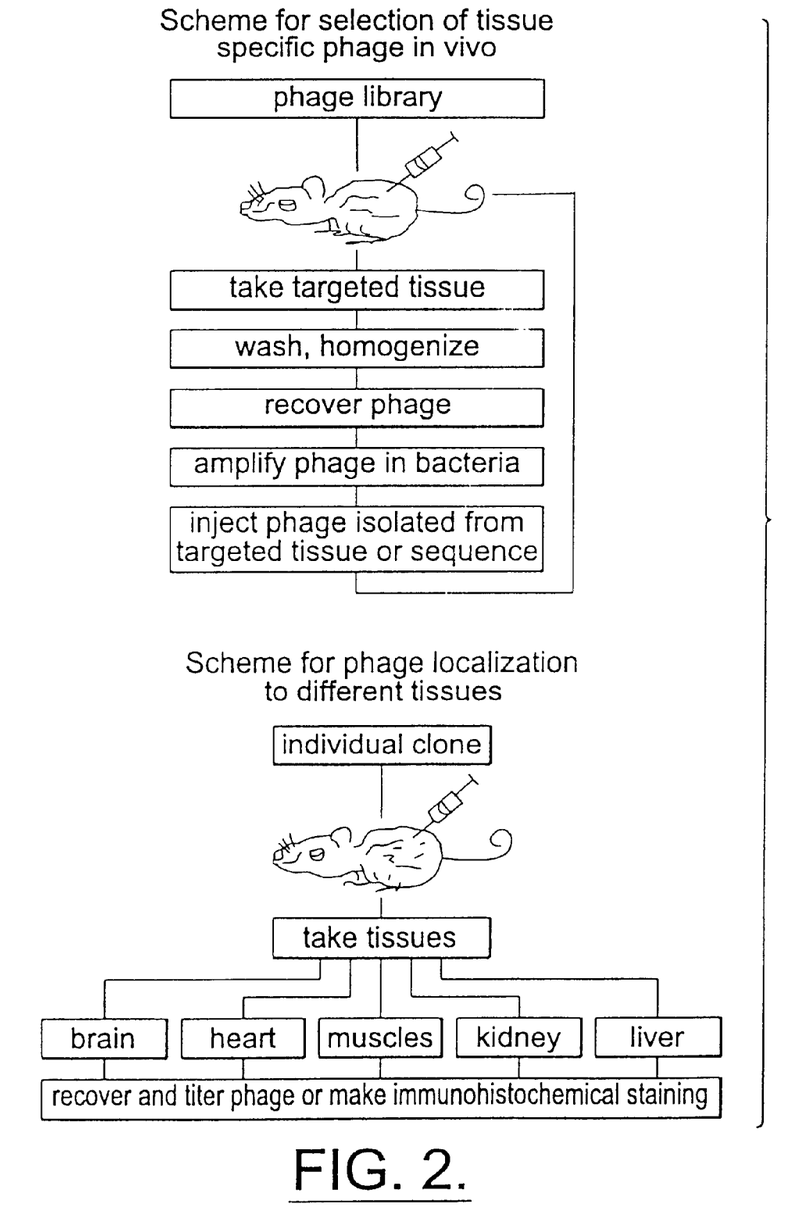
FIG. 2 provides the scheme for selection of tissue-specific phage in vivo.

In round one of selection, the phage library is injected intravenously and multiple tissues may be recovered. In subsequent rounds, the phage purified from specific tissues recovered in round one is injected intravenously, and thus, only that tissue is recovered. In rounds 2–4, separate animals are needed for each tissue being examined. After the last round, the phages are plated on a lawn of bacteria and a number of phage plaques are isolated and the DNA sequenced. Of these a certain percentage will represent the dominant selected clone. FIG. 2 provides a scheme for selection of tissue specific phage.

Therefore, muscle-specific peptides can be identified which will bind to, and be internalized by, the target cells. Specific peptides sequences include:

WDA NGK T (Trp-Asp-Ala-Asn-Gly-Lys-Thr)
ASS LNI A (Ala-Ser-Ser-Leu-Asn-Ile-Ala)
MST QSI N (Met-Ser-Thr-Gln-Ser-Ile-Asn)
SQL PAY P (Ser-Gly-Leu-Pro-Ala-Tyr-Pro)
GET RAP L (Gly-Glu-Thr-Arg-Ala-Pro-Leu)
CGH HPV YAC (Cys-Gly-His-His-Pro-Val-Tyr-Ala-Cys)
QWH GPL H (Gln-Trp-His-Gly-Pro-Leu-His)
HVH TLP T (His-Val-His-Thr-Leu-Pro-Thr)
MHH TRF Y (Met-His-His-Thr-Arg-Phe-Tyr) the sequences set forth in SEQ ID NO:1, SEQ ID NO:2, SEQ ID NO:8, SEQ ID NO:9, SEQ ID NO:29, SEQ ID NO:21, SEQ ID NO:24, SEQ ID NO:25, and SEQ ID NO:26, respectively. See, also Table 1 for further in vivo selection results.

TABLE 1

| SEQUENCE | TISSUE | ANIMAL | NUMBER OF PHAGE CLONES SEQUENCED | FREQUENCY | REMARKS (Selection details) |
| --- | --- | --- | --- | --- | --- |
| ASSLNIA (SEQ ID NO: 2) | skeletal muscle | mouse | 10 | 40 | 3 in vitro rounds on $C_2C_{12}$ myotubes (differentiated myoblasts) followed by 2 in vivo rounds on skeletal muscle |
| WDANGKT (SEQ ID NO: 1) | skeletal muscle | mouse | 27 | 19 | 4 in vivo round sin skeletal muscle |
| WDANGKT (SEQ ID NO: 1) | skeletal muscle | mouse + dog | 10 | 10 | 2 in vitro on $C_2C_{12}$ myotubes followed by 2 in vivo rounds on skeletal muscle |
| GETRAPL (SEQ ID NO: 27) | skeletal muscle | mouse | 27 | 37 | 4 in vivo rounds in skeletal muscle |
| GETRAPL (SEQ ID NO: 29) | neuro musclar | mouse | 34 | 12 | 4 in vivo rounds in neural muscular tissue |
| CGHHPVYAC (SEQ ID NO: 21) | skeletal muscle | dog | 20 | 100 | 3 in vivo rounds in cardiac muscle. This sequence represents a cyclic peptide where the C residues join to form a ring structure |
| CGHHPVYAC (SEQ ID NO: 21) | cardiac muscle | dog | 40 | 20 | 3 in vivo rounds in cardiac muscle |

TABLE 1-continued

| SEQUENCE | TISSUE | ANIMAL | NUMBER OF PHAGE CLONES SEQUENCED | FREQUENCY | REMARKS (Selection details) |
|---|---|---|---|---|---|
| SGTLFAN (SEQ ID NO: 22) | cardiac muscle | dog | 40 | 28 | 3 in vivo rounds in cardiac muscle |
| KAPLTPV (SEQ ID NO: 23) | cardiac muscle | dog | 40 | 8 | 3 in vivo rounds in cardiac muscle |
| QWHGLPLH (SEQ ID NO: 24) | cardiac muscle | mouse | 36 | 20 | 3 in vivo rounds in cardiac muscle |
| HVHTLPT (SEQ ID NO: 25) | cardiac muscle | mouse | 36 | 11 | 4 in vivo rounds in cardiac muscle |
| MHHTRFY (SEQ ID NO: 26) | cardiac muscle | mouse | 36 | 8 | 4 in vivo rounds in cardiac muscle |

In the Table, "Four rounds of selection . . . ," means that in round 1, the phage library was injected intravenously, and a specific tissue was recovered. In round 1, multiple tissues are recovered from one animal (skeletal muscle, cardiac muscle, etc.). In any subsequent round, the phage purified from a specific tissue is injected intravenously, and only that tissue is recovered. Thus, in rounds 2–4, separate animals are needed for each tissue being examined. After the last round, the phage are plated on a lawn of bacteria and a number of phage plaques are isolated and the DNA sequenced. This is represented in the Table by "number of phage clones sequenced." Of these, a certain percentage will represent the dominant selected clone. For example, 4 of 10 plaques in the first experiment revealed the ASSLNIA peptide, giving a frequency of 40%.

The experiments disclosed herein, represent the first in vivo selection in any species other than mouse. Generally, phage was left to circulate for one hour.

Peptide APVHRPL (SEQ ID NO: 27) was selected via two rounds in vivo, in canine cardiac muscle. The clone was found in the washed tissue fraction and may represent a very high affinity ligand.

HAIYPRH (SEQ ID NO: 28) was selected via four rounds in vivo, in murine muscle, at a low frequency (4%). This clone may represent a significant muscle binding peptide.

The frequency of appearance of each amino acid within the library is known. Thus, the frequency of amino acids within the pool of selected peptides can be compared. A number of amino acids have been observed to be over-represented. These amino acids, (H, A, G, V, S, Y, T, N, R) may be significant for muscle binding. Such amino acids may play a role in consensus sequences that are important for binding. One of skill in the art may identify consensus sequences by analysis as well as construction of synthetic sequences and testing binding.

Example 3

Selection of A Panel of Muscle-binding Peptides

Figure 3:
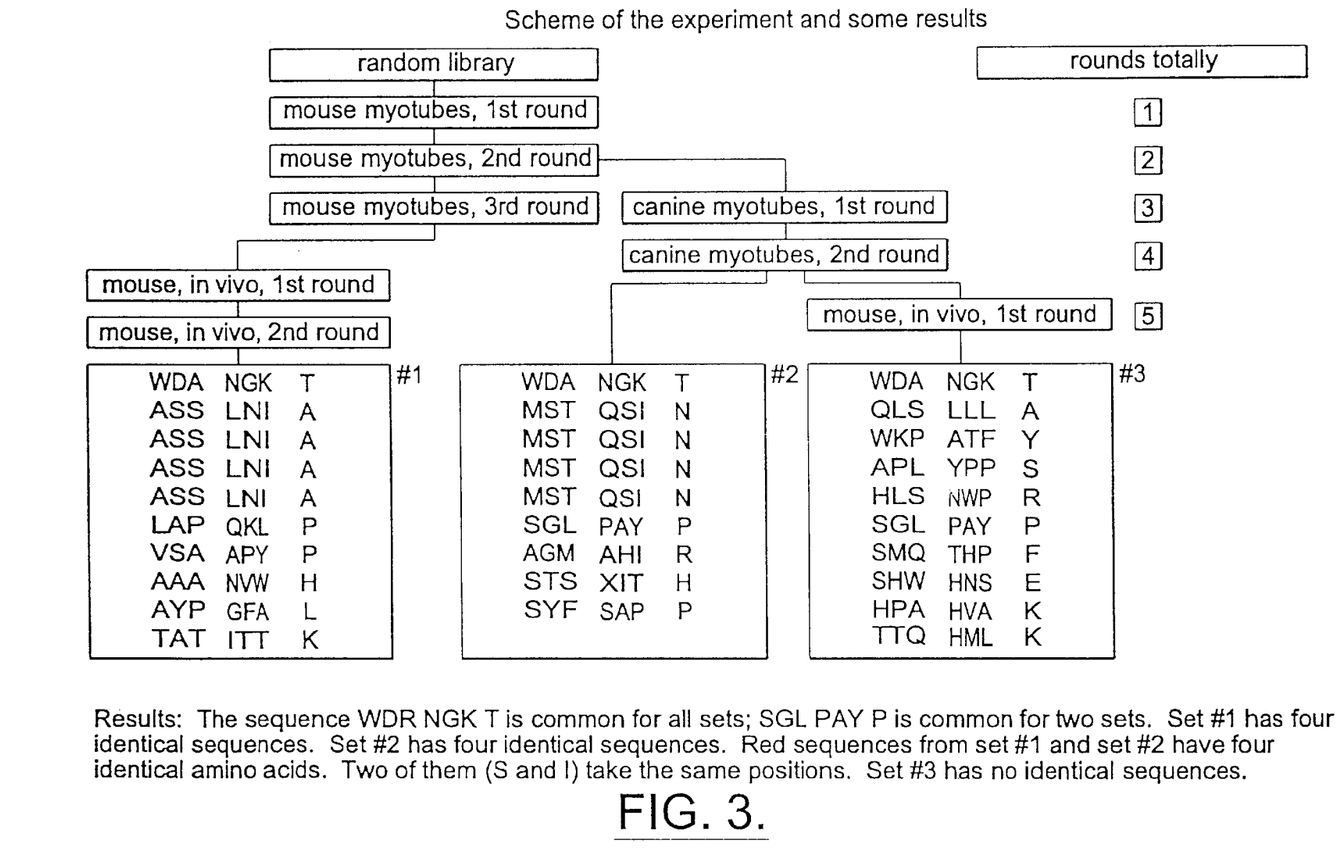
FIG. 3 provides the experimental scheme and results. The sequences shown in the Figure are set forth in SEQ ID NO: 1 (WDANGKT), SEQ ID NO: 2 (ASSLNIA), SEQ ID NO: 3 LAPKQLP), SEQ ID NO: 4 (VSAAPYP), SEQ ID NO: 5 (AAANVWH), SEQ ID NO: 6 (AYPGFAL), SEQ ID NO: 7 (TATITTK), SEQ ID NO: 8 (MSTQSIN), SEQ ID NO: 9 (SGLPAYP), SEQ ID NO: 10 (AGMAHIR), SEQ ID NO: 11 (STSXITH), SEQ ID NO: 12 (SYFSAPP), SEQ ID NO: 13 (QLSLLLA), SEQ ID NO: 14 (WKPATFY), SEQ ID NO: 15 (APLYPPS), SEQ ID NO: 16 (HLSNWPR), SEQ ID NO: 17 (SMQTHPF), SEQ ID NO: 18 (SHWHNSE), SEQ ID NO: 19 (HPAHVAK) and SEQ ID NO: 20 (TTQHMLK).

The peptides identified in Example 2 will be further characterized as described below in Section iii. In addition, a larger panel of muscle-binding peptides will be isolated to increase the likelihood that the most specific and highest affinity muscle-targeting peptides will be identified. Peptides of longer amino acid sequences will also be tested. See FIG. 3 for an overall scheme for peptide selection.

i. Selection of Muscle-binding Peptides

Using phage libraries (such as those presented on pIII, 15- and 20-mers presented on pVIII), a variety of myotube-binding peptides will be selected. Multiple muscle targets will be selected against to identify common muscle-binding peptides and increase the likelihood of identifying a wide panel of peptides. Peptides will be selected against differentiated mouse $C_2C_{12}$ and So 18 myotube cell lines and against primary muscle samples from mouse, rat and dog quadricep, tibialis anterior, and soleus muscles. A phage selection strategy will be employed to identify peptides which target endocytosing receptors. Selection will be carried through sufficient cycles until increased binding by the population is observed or sequencing of phage clones indicates that the population has collapsed down to a finite number of peptide clones. Clones from this round (round N) will be screened as described below in section iii. Clones from the round N-1 will also be tested, since it is conceivable that truly cell-specific peptides may only transiently appear in the selection process and may be out-competed by less specific, higher affinity/avidity peptides in later rounds of selection. If selection against myotubes does not yield any useful peptides, then selection and screening will be carried out against myoblast cell lines or fresh myoblast isolates.

ii. Selection of Muscle-binding Peptides with New Libraries

While useful peptides have already been isolated from a 20-mer library and a 7-mer library, it should be noted that any one library vastly under-represents the total number of possible random 20-mer peptides. There is a "space" of $\sim 10^{26}$ possible 20-mer peptides. Our one library presents $\sim 10^8$ peptides and therefore represents only 1 in $10^{18}$ of these possible 20-mers. The number of phage clones is the limitation to how many peptides a library can contain. Therefore, production of more $10^8$ transformant peptide will produce entirely independent peptides to be screened (up to $10^{18}$ could in theory be created). It is not known that 20 amino acids are required for cell-binding, however, the 20-mer libraries out complete 12-mer libraries for selection against a variety of cell targets (Barry et al. (1996) Mature Medicine 2:299–305; and not shown). This suggests large peptides are better for cell binding/entry and that peptides even larger than 20 amino acids may be useful. An additional benefit is derived by using large peptide libraries, since any one 20-mer peptide also represents 14 6-mer peptides, 12 8-mer peptides etc. Given these features, new 20-mer and larger libraries will be created on pill and pVIII to increase the probability that novel, useful peptides can be identified. New 20-mer libraries will be created using randomly synthesized oligonucleotides (Barry et al. (1996) Mature Medicine 2:299–305). To create even larger peptide libraries, genomic DNA from E. coli or mammalian sources will be randomly sheared to small fragments (~200 base pairs), blunted, and cloned into pIII or pVIII. Once created, these libraries will be selected as in section i and screened as in section iii.

iii. Rapid Screening of Peptide Ligands with a Hepttageptide Phage Display Library a. Ph.D.™ Phage Display Peptide Library (New England Biolabs) is a ligand screening system which is based on a combinatorial library of random peptide 7-mers fused to a minor coat protein (piii) of the filamentius coliphage M13.

b. The heptapeptide library consists of $2\times10^9$ electroporated sequences amplified once to yield≈100 copies of each sequence in 10 µl of the supplied phage.

c. Phage display creates a physical linkage between a selectable function (the displayed peptide sequence) and the DNA encoding that function.

d. This allows rapid identification of peptide ligands for a variety of receptor target molecules by an in vitro selection process called biopanning.

e. Biopanning is carried out by simply passing the pool of phage displayed peptides over a plate coated with the target, washing away the unbound phage, and eluting the bound phage.

Advantages a. Unlike the use of known ligands, the process requires no prior knowledge of the biology of the target cells.

b. Molecular recognition and selection are not influenced by the immunogenicity of candidate targets.

c. As a result, peptide ligands should be more easily isolated and incorporated into biological vectors by cloning or by chemical conjugation to synthetic vectors.

iv. Screening Peptides for Specificity

Candidate peptides generated in sections ii and iii will be screened for specific binding to myotubes. Initial screens will compare the binding of these peptides on phage against the myotube lines $C_2C_{12}$ and So 18 and against heterologous cell lines including fibroblasts, macrophages, dendritic cells, and hepatocytes. Peptides will be screened not only for binding muscle cells, but also for low-level binding to hepatocytes (cell lines and primary isolates), since the liver is a tremendous sink for adenovirus in vivo. The liver would therefore be a tissue to avoid targeting with new peptides. Likewise, peptides will be screened for low binding to macrophage and dendritic cells. It is likely that delivery of potentially immunogenic gene products and vector antigens to these potent antigen-presenting cells would increase the problem of immune-dependent destruction of adenovirus-transfected cells (Yang et al. (1996) *Gene Therapy* 3:412–420).

Some of the current immunogenicity of adenovirus vectors could be due to low-level infection of similar antigen-presenting cells. If so, selected peptides that give lower binding than wild-type fiber protein to these immune cells might actually attenuate the existing immune responses against adenovirus-transfected cells.

v. Optimization of Peptides by Mutagenesis

As described in section ii, the phage libraries vastly under-represent all possible peptides within a particular library. That any peptides can be selected to bind cells would seem remarkable with only this information. Conversely, this poor representation implies that any peptide selected to bind a cell has only a $10^{-18}$ chance of being "the" optimal peptide for binding its target. Therefore, it is likely that any of these lead peptides can be improved by random mutagenesis. Mutagenic libraries will be constructed by insertion of randomly mutated oligonucleotides based on the candidate peptide's sequence into the pIII or pVIII gene in phagemid vector fAFF1 or p8V2 (Barry et al. (1996) *Mature Medicine* 2:299–305). Random insertion of mutant bases in positions 1 and 2 of each codon will be constrained at a ratio of 70:10:10:10 such that 70% of each will contain the normal base and 30% will contain another base. The third position of each codon will be restricted to G or T as described previously (Barry et al. (1996) *Mature Medicine* 2:299–305). Once generated, these libraries will be panned as previously performed (Barry et al. (1996) *Mature Medicine* 2:299–305) and consensus amino acids will be identified by sequencing a pool of selected mutant peptide-presenting phage. In addition, the optimal sequence will be determined as described in sections i and iv.

Example 4

Vertebrate Animals

Inbred Balb C mice will be used to screen phage presentation libraries. Additional mice will be used following a similar protocol to assay the ability of novel peptide ligands cloned into fiber knob, and into recombinant adenoviruses to bind to muscle. The phage library will be injected intravenously under deep halothane anesthesia. At periods of time ranging from 5 to 30 minutes, the mice will be euthanized by cervical dislocation and immediately immersed in liquid nitrogen. Approximately 20 mice will be allowed to recover from anesthesia following intravenous injection, and euthanized at two days to one week following injection to assess the localization of recombinant adenovirus gene expression.

The initial use of the mouse allows a larger number of potential muscle-specific binding motifs to be screened than would a larger animal model. Initial screens will utilize myoblast and myotube cultures; however, the fetal/neonatal gene expression pattern of these cells while in culture may not permit the isolation of binding moieties appropriate for adult skeletal muscle. Thus, the use of in vivo screening of phage libraries will significantly shorten the interval involved in discovery of these novel binding moieties. Subsequently, the ability of modified fiber, and then of modified adenovirus to specifically target muscle after intravenous injection can only be tested in vivo. The use of the M-PFK deficient dog model provides a readily assessable animal model of a myopathy in which the ability of tropism modified adenovirus to deliver a therapeutic gene can be investigated. (See Example 5).

Example 5

Therapy in a Canine Model i. Pre-treatment Studies

Neonatal dogs (1 day to 1 week old) from an M-PFK colony will be tested for M-PFK deficiency using the PCR-based allele-specific test that we devised. Five juvenile (4–9 months) dogs, which have been determined to be homozygous mutant for M-PFK deficiency, will be used in this study. Each dog will have skeletal muscle biopsies taken from the gastrocnemius and triceps muscles. Portions of these biopsies will be frozen and evaluated histochemically. Tissue samples will also be homogenized and assayed for M-PFK activity. Detailed medical records are kept on all colony animals, and any episodes of anemia or pigmenturia will be recorded. Pre-treatment magnetic resonance spectroscopy (MRS) studies will be performed on each animal to establish parameters for these investigations. Whole blood and muscle will be frozen at −70° C. to provide pre-treatment controls for Southern hybridizations, PCR amplification of vector sequences, PFK activity studies, and M-PFK-specific immunoblots. Serum samples will be frozen as controls for the antigenicity studies described below.

ii. In vivo Gene Delivery to M-PFK Deficient Dogs

After completion of the pre-treatment studies, each dog will be sedated, and a 21 gauge intravenous catheter placed in the cephalic vein. Tropism-modified vectors comprising the peptides and expression cassettes containing M-PFK will be delivered as a slow injection. During injection, the dogs will be monitored for signs associated with adverse reactions such as anaphylaxis, and should such reactions occur, administration of the vector will be suspended and appropriate treatments initiated.

iii. Studies to Detect the Transferred Canine M-PFK cDNA

Skeletal muscle biopsies will be taken from the contralateral gastrocnemius and triceps muscle at one, two, three, four, six and eight weeks following the injection of the vector, and monthly thereafter. DNA will be recovered from this tissue sample and examined by PCR for the transferred virus.

iv. Immunological Detection of Tissue Specific Expression of M-PFK

To determine if the vector which has been transferred to the muscle is expressing M-PFK, M-PFK specific immunoblots will be performed. One hundred to one hundred fifty micrograms of protein are loaded into each well of a 7.5% polyacrylamide gel. Following electrophoresis the gel is stained with coomassie brilliant blue to show protein content, and the electrophoretically transferred to 0.45 micron nitrocellulose membranes. The membranes are blocked with 5% milk powder for 1 hr, followed by 0.05% Tween 20 for 30 min. The membranes are then incubated with the primary antibody, guinea pig anti-rabbit M-PFK, for 18 hr at room temperature, with gentle agitation. Three washes with Tris-buffered saline (0.2 M Tris, 5 M NaCl, pH 7.5; TBS), 30 seconds to one minute each, are followed by a 3 hr incubation with peroxidase-conjugated rabbit anti-guinea pig IgG (Sigma), at room temperature. A final three rinses in TBS are followed by the addition of 4 chloronaphthol to allow for color development.

V. Biochemical Detection of Enzyme Activity from Transferred M-PFK

To determine if the expressed M-PFK possesses enzymatic activity, the muscle biopsy samples will be evaluated by biochemical assay. Phosphofructokinase from muscle biopsies will be prepared for activity assay by homogenization for 15 seconds in 5 volumes of PFK extraction buffer [50 mM Tris-phosphate, pH 8.0, 25 mM NaF, 0.1 mM ethylenediamine-tetraacetic acid (EDTA), 25 mM $(NH_4)_2SO_4$, 1 mM adenosine triphosphate (ATP), 10 mM dithiothreitol (DTT), 0.5 mM phenylmethyl-sulfonyl fluoride (PMSF), 1 mM p-aminobenzamindine, 250 µg/liter Leupeptin, 0.1 mM Na-p-tosyl-L-lysine chloromethyl ketone]. The homogenate is then sonicated and centrifuged at 20,000×g for 1 hour. The supernatant is saved and stored at −20° C. Enzyme activity will be determined by a calorimetric reaction in 50 mM tris(hydroxymethyl) methylglycine, pH 8.4, 5 mM $MgCl_2$, 0.15 mM NADH, 0.1 mM DTT, 0.25 mM ATP, 2.4 mM Fructose-6-phosphate, 0.18 units aldolase, 0.6 units triose phosphate isomerase, and 0.1 unit glycerophosphate dehydrogenase. The decrease in absorbance at a wavelength of 340 nm is monitored for 10 min at 26° C. and one unit of PFK activity is defined as the amount of enzyme needed to convert 1 µmole of fructose-6-phosphate to fructose-1, 6-diphosphate in one minute. All studies will be compared to pretreatment values as well as values from ag-matched normal and M-PFK deficient dogs, and dogs treated with a control vector.

vi. Histochemical Localization of Tissue-specific Expression of M-PFK

Determination of the number and type of muscle cells expressing M-PFK activity will be performed by histochemical staining for M-PFK. Briefly, small pieces of muscle, frozen in liquid nitrogen-cooled isopentane, will be mounted in a cryostat and sectioned at 6 microns. These sections will be placed on microscope slides, dried, and incubated in a solution containing 10 mM $Na_2HAsO_4$, 2 mM fructose-6 phosphate, 1 mM diphosphopyridine nucleotide (DPNH) 1 mM ATP, 1 mM $MgSO_4$, and 4 mg/ml NBT. The present of PFK activity is seen as a dark blue stain within the cells.

vii. Evaluation of the Efficacy of Gene Transfer in Treating M-PFK Deficiency

To evaluate the suitability of the molecular conjugate vectors for treating inherited myopathies, the effects of treatment on the clinical signs of M-PFK deficiency will be evaluated. The dogs will be observed closely for signs of myopathy, including fatigue, exercise intolerance, and muscle cramping. Light levels of long duration exercise such as walking will be used to attempt to induce signs of myopathy. If stable expression is seen in muscle biopsy specimens exceeding one month post injection, MRS studies will be performed to determine the effect of M-PFK expression on the metabolic block. With the dog placed under general anesthesia, the muscle will be tetanically stimulated and the level of inorganic phosphorus determined. The results of these studies will be compared to the pretreatment values to determine the extent of improvement in muscle function. Additionally, the dogs will be closely observed during this procedure for episodes of cramping or muscle contracture.

viii. Detection of Immune Response to the Adenoviral Vector

To determine if the vectors induce an immune response in the animal being treated, serum samples taken prior to treatment and each biopsy will be hybridized with nitrocellulose blots of adenoviral proteins run on SDS polyacrylamide gels. A secondary, labeled anti canine IgG will be utilized to visualize any canine anti-adenoviral antibodies. Antibodies to the transferred M-PFK gene are not expected as the canine M-PFK will be used and the deficiency is due to a point mutation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated peptide, wherein said peptide is 7 amino acids to 20 amino acids, comprising an amino acid sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29.

2. The peptide of claim 1, wherein said peptide is capable of binding muscle cells in vivo.

3. The peptide of claim 2, wherein said peptide is a muscle-type specific peptide.

4. The peptide of claim 3, said muscle-type specific peptide comprising an amino acid sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

5. The peptide of claim 3, wherein said peptide is capable of binding specific muscle cells selected from the group consisting of smooth, skeletal, and cardiac muscle cells.

6. The peptide of claim 3, wherein said peptide is a species specific peptide.

7. The peptide of claim 3, wherein said peptide is a species independent peptide.

* * * * *

UNITED STATES PATENT AND TRADEMARK OFFICE
CERTIFICATE OF CORRECTION

| | |
|---|---|
| PATENT NO. | : 6,329,501 B1 |
| DATED | : December 11, 2001 |
| INVENTOR(S) | : Smith et al. |

It is certified that error appears in the above-identified patent and that said Letters Patent is hereby corrected as shown below:

<u>Column 8,</u>
Table 1, under "SEQUENCE", line 8, "27" should read -- 29 --.

<u>Column 9,</u>
Table 1-continued, under "SEQUENCE", line 5, "QWHGLPLH" should read -- QWHGPLH --.

Signed and Sealed this

Fourth Day of June, 2002

*Attest:*

JAMES E. ROGAN
*Attesting Officer*  *Director of the United States Patent and Trademark Office*